United States Patent [19]

Nathan et al.

[11] Patent Number: 5,342,322
[45] Date of Patent: Aug. 30, 1994

[54] NEEDLE COVER ASSEMBLY FOR SYRINGES

[75] Inventors: Rasa N. Nathan, 214 N. Elm Dr., Beverly Hills, Calif. 90210; Paul Thomas, San Pedro, Calif.

[73] Assignee: Rasa N. Nathan, Beverly Hills, Calif.

[21] Appl. No.: 162,240

[22] Filed: Dec. 6, 1993

Related U.S. Application Data

[63] Continuation-in-part of Ser. No. 63,946, May 20, 1993.

[51] Int. Cl.$^5$ ............................................. A61M 5/32
[52] U.S. Cl. ..................................... 604/192; 604/263
[58] Field of Search ............... 604/192, 187, 198, 263, 604/110

[56] References Cited

U.S. PATENT DOCUMENTS

| | | |
|---|---|---|
| 4,820,277 | 4/1989 | Norelli . |
| 4,838,871 | 6/1989 | Luther . |
| 4,886,503 | 12/1989 | Miller . |
| 4,909,792 | 3/1990 | Norelli . |
| 4,950,249 | 8/1990 | Jagger et al. . |
| 4,966,591 | 10/1990 | Yuen . |
| 5,011,475 | 4/1991 | Olson . |
| 5,055,102 | 10/1991 | Sitnik . |
| 5,188,611 | 2/1993 | Orgain ................................. 604/192 |
| 5,207,653 | 5/1993 | Janjua et al. ....................... 604/192 |

*Primary Examiner*—John D. Yasko
*Attorney, Agent, or Firm*—Thomas I. Rozsa; Tony D. Chen

[57] ABSTRACT

The present invention is an improved needle cover assembly for a syringe. The needle cover assembly includes a first half and an opposite unequal second half with an arc shaped inner shell such that the first half encloses the arc shaped inner shell of the second half of the needle cover assembly. The arc shaped inner shell of the second half extends over the tip of the needle and the first half of the elongated cover member extends over both the arc shaped inner shell and the tip of the needle for providing double protection. The two halves of the needle cover assembly are attached to a frustum shaped base member such that a hollow hub member can be press-fitted into the frustum shaped base member. A rotatable collar surrounds the frustum shaped base member, and when the rotatable collar is rotated approximately 90°, the two halves of the cover member are split apart so that the two halves of the needle cover are away from each other, thereby exposing the needle so that it can be used for an injection of medicine. After the injection has been given, the two halves of the needle cover assembly can be closed by rotating the rotatable collar back to approximately 90°.

13 Claims, 5 Drawing Sheets

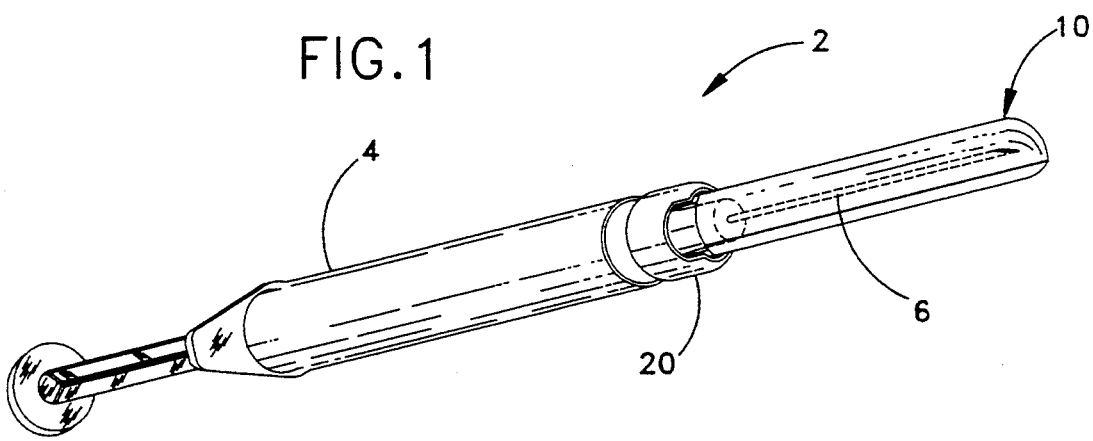
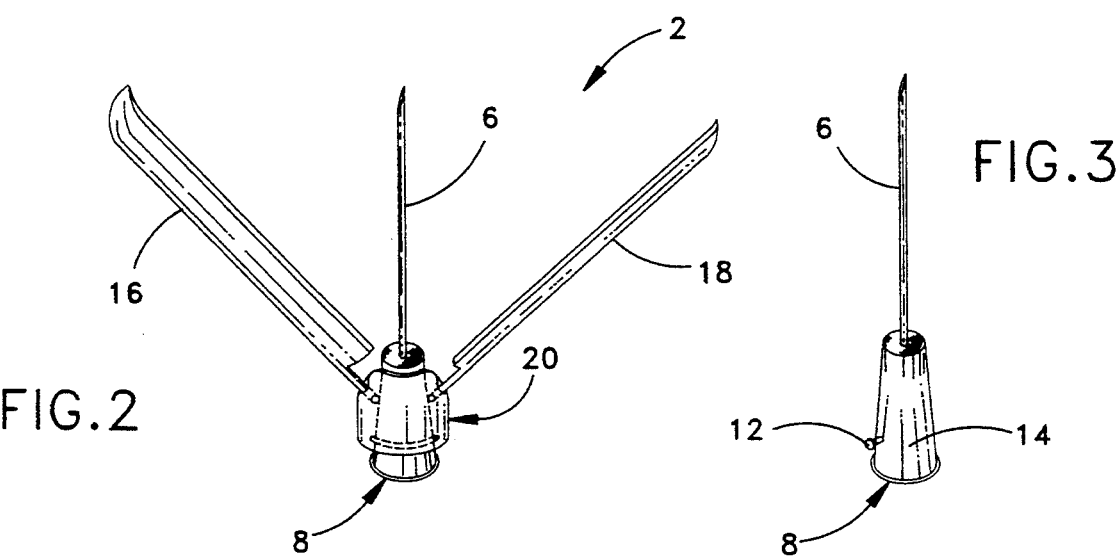
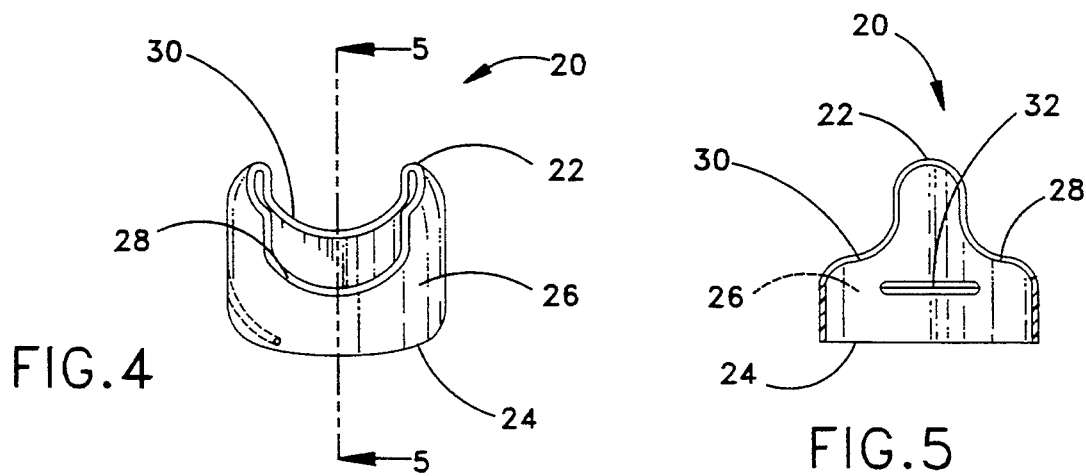

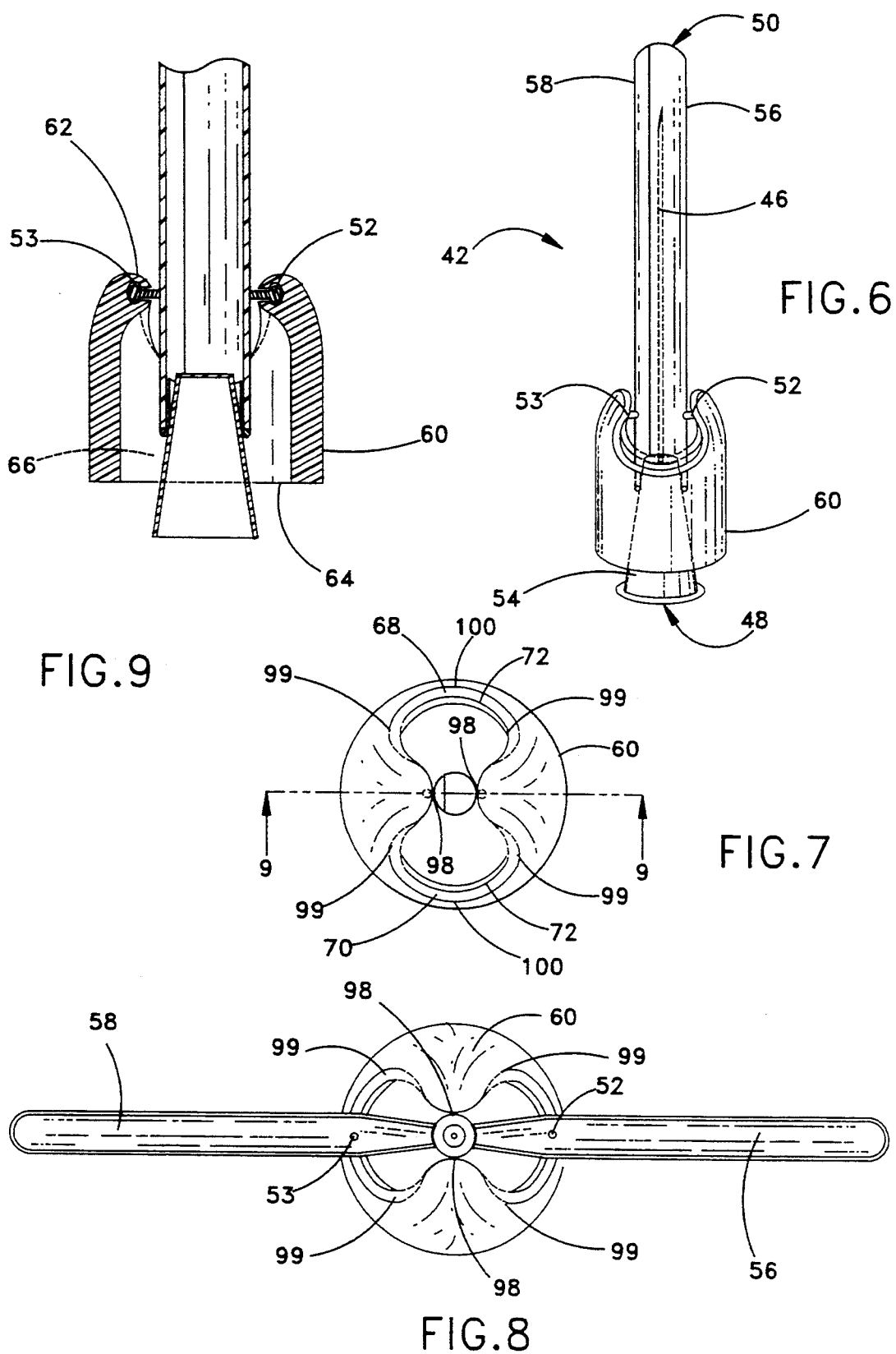

NEEDLE COVER ASSEMBLY FOR SYRINGES

This patent application is a continuation-in-part of patent application Ser. No. 08/063,946 filed on May 20, 1993, now pending.

BACKGROUND OF THE INVENTION

1. Field of The Invention

The present invention relates to the field of syringe needles. In particular, the present invention relates to needle cover assemblies for syringes.

2. Description of The Prior Art

A common problem frequently encountered in hospitals and other medical facilities where injections are given is that when the doctor or nurse recaps the cover back onto the hypodermic needle, there is a motion of the hypodermic needle advancing toward the person's hand holding the cover and sometimes when recapping the cover onto the hypodermic needle, they accidentally prick themselves. This is a serious problem today when the injection has been given to someone with a serious disease such as the well known Acquired Immuno Deficiency Syndrome (AIDS).

Conventional hypodermic needles provide no safe way for recapping the cover onto the hypodermic needle after use and consequently, used hypodermic needles are the most common cause of accidental prick injuries in hospital. This problem has led to the present invention needle cover assembly.

The following prior art references were found relevant to the field of the present invention.

1. U.S. Pat. No. 4,820,277 issued to Norelli on Apr. 11, 1989 for "Safety Cover For Syringe Needles" (hereafter "the Norelli '277 Patent").

2. U.S. Pat. No. 4,838,871 issued to Luther on Jun. 13, 1989 for "Needle Guard, And Assembly" (hereafter "the Luther Patent").

3. U.S. Pat. No. 4,886,503 issued to Miller on Dec. 12, 1989 for "Disposable Covered Needle For Syringe" (hereafter "the Miller Patent").

4. U.S. Pat. No. 4,909,792 issued to Norelli on Mar. 20, 1990 for "Safety Cover For Syringe Needles" (hereafter "the Norelli '792 Patent").

5. U.S. Pat. No. 4,950,249 issued to Jagger et al. on Aug. 21, 1990 for "Hypodermic Needle With Reclosable Safety Cap" (hereafter "the Jagger Patent").

6. U.S. Pat. No. 4,966,591 issued to Yuen on Oct. 30, 1990 for "Needle Assembly" (hereafter "the Yuen Patent").

7. U.S. Pat. No. 5,011,475 issued to Olson on Apr. 30, 1991 for "Protector For Intravenous And Syringe Needles" (hereafter "the Olson Patent").

8. U.S. Pat. No. 5,055,102 issued to Sitnik on Oct. 8, 1991 for "Swing-Away Disposable Syringe Needle Cover" (hereafter "the Sitnik Patent").

The Norelli '277 Patent discloses a safety cover for a conventional needle. It includes a pair of elongated semi-cylindrical jaws which cooperate to completely encase a conventional needle. Each jaw is hingeably attached to the syringe barrel. When the jaws are opened, the jaws are generally parallel to each other and adjacent to the syringe. The two jaws are symmetrically split.

The Luther Patent discloses an assembly of a needle guard for a hub and attached needle. It includes an elongated cylindrical guard member mounted on the hub. The cylindrical guard member defines a longitudinal slot which coincides with the needle. The guard member can be rotated away from the needle when in use.

The Miller Patent discloses a disposable covered needle for a syringe. It includes a needle member and a cover member pivotably connected to each other. The cover member has a long narrow opening for the needle to pass through when the cover member is pivoted away and is covered by a rupturable plastic film which breaks when the cover is pivoted to expose the needle.

The Norelli '792 Patent discloses a safety cover for syringe needles similar to the Norelli '277 Patent.

The Jagger Patent discloses a hypodermic needle apparatus. The needle cap is split longitudinally into two halves which, in the closed position, abut each other. A ring is used to hold the two halves in the closed position. The ring is threadedly mounted on a threaded portion of the hub which extends upwardly from a base which is used to attach the apparatus to a conventional syringe. The two halves spring outwardly into the perpendicular position when in use. The two halves are symmetrically split and can be rotated to lock and unlock the two halves.

The Sitnik Patent discloses a swing-away disposable syringe needle cover. It includes a tube which is closed on one end and has a longitudinal slit at the other end, which is sufficiently long and wide to permit the needle to traverse through the slit laterally. The tube cover is rotated to the perpendicular position to expose the needle.

The Yuen Patent discloses a needle assembly for withdrawing body fluids. The two cover elements are pivotally connected to the body for rotation toward and away from each other in a plane containing the needle about two pivot points. The two cover elements spring outwardly into the perpendicular position. Each cover element has two halves which are symmetrically split.

The Olson Patent discloses a projector assembly. It includes an elongated hollow protective sheath mounted on the hub and having openings extending longitudinally along both sides thereof to permit the needle to be inserted into one of two conduits. The top of the protective sheath has an opening.

Therefore, the purpose of the present invention is to eliminate the situation where someone has a hypodermic needle which is required to be in motion toward a person's hand when the cover is to be recapped onto the hypodermic needle. In addition, there is a need for an improved needle cover assembly which simplifies the recapping of the cover onto the hypodermic needle and provides double protection.

SUMMARY OF THE INVENTION

The present invention is a needle cover assembly for a syringe. The present invention relates to a two-part needle cover assembly. One part of the cover extends over the head of the needle so that the split is not symmetrically down the middle of the cover but is instead along an arc greater than 180°. Therefore, there are two halves to the needle cover assembly but they are asymmetrical; for example they may be around 270° or so for one part and 90° for the other part.

The two halves of the needle cover assembly are hingeably attached to a hollow hub. A rotatable collar surrounds the hollow hub. When the rotatable collar is rotated by 90°, the two halves are able to break apart so that the portions of the needle cover are away from each other, thereby exposing the needle so that it can be used for injecting a person with medicine. After the injection has been given, the two halves of the needle cover assembly can be closed by rotating the rotatable collar 90°.

It has been discovered, according to the present invention, that by utilizing a hypodermic needle within the needle cover assembly, it will provide a safe and easy way to install the hypodermic needle onto the syringe without the danger of the user being accidentally pricked by the hypodermic needle.

It has also been discovered, according to the present invention, that if the needle cover assembly is made with a cover comprising two unequal halves, it will provide a way to split the cover to inject the medicine into a patient while at the same time covering the tip of the needle when it is not in use.

It has additionally been discovered, according to the present invention, that if the needle cover assembly is made with a rotatable collar, it will provide a way to open and close the cover.

It has further been discovered, according to the present invention, that if the collar of needle cover assembly has a locking groove in the interior surface of the collar, it will provide a unique way of rotating the collar to open or close the cover on the needle cover assembly.

It has also been discovered, according to the present invention, that in prior art covers where the two halves are equal, they come together in line with the tip of the needle and a crack at their area of joinder permits a user to accidentally prick himself even when the cover is closed. It has been discovered that by making the halves uneven such that the large half covers the needle in the closed position, this problem is eliminated.

It is therefore an object of the present invention to provide an improved needle cover assembly for a syringe.

It is an additional object of the present invention to provide a needle cover assembly which is simple in design and inexpensive to manufacture and which can be safe and easy to use.

It is a further object of the present invention to provide a needle cover assembly which can be connected to a syringe by pushfit or threaded means.

It is an additional object of the present invention to provide a needle cover with a split cap that is unevenly split so that one of the uneven halves covers the tip of the needle when the needle is not in use and facilitates easy recovering of the needle including covering the tip after the needle has been used.

It is another object of the present invention to provide a simple and efficient way to expose the needle by having the unequal halves of the cover rotate away from each other, and then recover the needle by having the unequal halves rotate toward each other back to the closed position, to thereby eliminate any possible motion of the exposed needle toward a user's finger when it is being recovered. In addition, the tip of the needle is covered by one unequal half so that the tip cannot possibly protrude through the split halves of the cover, even in the closed position.

Still another embodiment of the present invention needle cover assembly for a syringe relates to a four-part needle cover assembly. The four-part needle cover assembly includes a frustum shaped base member, a rotatable collar member, and a first half and an opposite unequal second half of a cover member. The opposite unequal second half has an arc shaped inner shell with reduced dimensions such that the first half encloses the arc shaped inner shell of the second half. The arc shaped inner shell extends over the tip of the needle while the first half extends over both the arc shaped inner shell and the tip of the needle to provide double protection.

The two halves of the needle cover assembly are pivotally attached to the frustum shaped base member such that a hollow hub member can be press-fitted onto the frustum shaped base member. The rotatable collar encloses the frustum shaped base member, and when the rotatable collar is rotated approximately 90°, the two halves of the cover member will split apart so that the two halves of the needle cover are away from each other, thereby exposing the needle so that it can be used for an injection of medicine. After the injection has been given, the two halves of the needle cover assembly can be closed by rotating the rotatable collar back to approximately 90°.

Still another embodiment of the present invention needle cover assembly for a syringe relates to a living hinge in which the first half and the opposite unequal second half of the cover member are hingeably and integrally attached to the frustum shaped base member.

It has also been discovered, according to the present invention, that if a needle cover assembly includes a rotatable collar member with an annular locking groove which engages with a frustum shaped base member, then it will provide a unique way of interlocking the rotatable collar member to the frustum shaped base member and thereby prevent portions of the needle cover assembly from becoming loosened.

It has additionally been discovered, according to the present invention, that if the rotatable collar member has smooth curved or spiral shaped channels at locations opposite to each other, then it will provide a unique way to open and close the first and second halves of the cover member.

It has further been discovered, according to the present invention, that in prior art covers where the two halves are equal, when they come together in line with the tip of the needle, a crack at the area permits a user to accidentally prick himself even when the cover is closed. It has been discovered that by making the halves uneven such that the small half has an arc shaped inner shell which covers the needle in the closed position, and the large half covers both the arc shaped inner shell of the small half and the needle in the closed position, a double protection is provided.

It has additionally been discovered, according to the present invention, that if the first and second halves of the cover member are integrally hingeably attached to the frustum shaped base member, then the molding and assembling costs in the manufacture of the product are significantly reduced.

It is therefore an additional object of the present invention to provide a needle cover assembly with a rotatable collar member which has an annular locking groove, so that a unique locking mechanism is provided to secure the rotatable collar member to the frustum shaped base member.

It is still an additional object of the present invention to provide a rotatable collar member with smooth curved or spiral shaped channels, so that it can easily open and close the first and second halves of the cover member of the needle cover assembly.

It is still a further object of the present invention to provide a simple and efficient way to expose the needle by having both halves of the cover rotate away from each other, and then re-cover the needle by having both halves rotate toward each other back to the closed position, to thereby eliminate any possible motion of the exposed needle toward a user's finger when the needle is being re-covered. In addition, the tip of the needle is covered by both the arc shaped inner shell of the second half and the arc of the first half of the cover member so that the tip cannot possibly protrude through the split portions of the cover member.

It is still an additional object of the present invention to provide living hinges to the first and second halves of the cover member such that they are integrally hingeably attached to the frustum shaped base member, so that the molding and assembling costs in manufacturing the needle covers are significantly reduced.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a perspective view of the preferred embodiment of the present invention needle cover assembly connected to a syringe.

FIG. 2 is a perspective view of the needle cover assembly with the two halves in the open condition.

FIG. 3 is a perspective view of a hypodermic needle attached to a hub member and a protruding flange extending outwardly from the hub member.

FIG. 4 is an enlarged perspective view of the rotatable collar member with two recess notches.

FIG. 5 is an enlarged cross-sectional view taken along line 5—5 of FIG. 4.

FIG. 6 is a perspective view of an alternative embodiment of the present invention needle cover assembly connected to a syringe.

FIG. 7 is a top plan view of the alternative embodiment of the present invention needle cover assembly in the closed position.

FIG. 8 is a top plan view of the alternative embodiment of the present invention needle cover assembly in the open position.

FIG. 9 is an enlarged cross-sectional view taken along line 9—9 of FIG. 7.

DESCRIPTION OF THE PREFERRED EMBODIMENT

Figure 10:
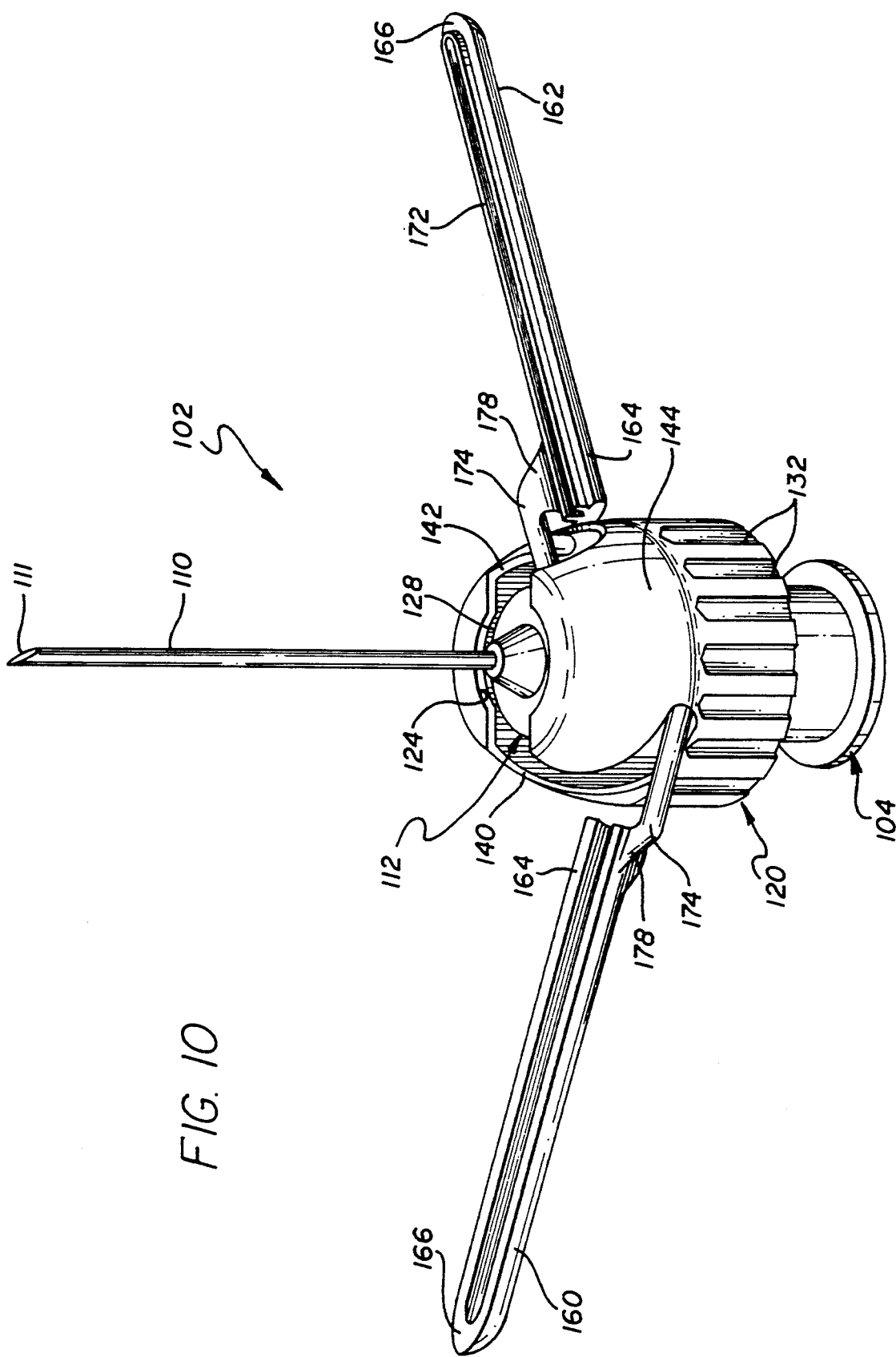
FIG. 10 is a perspective view of an alternative embodiment of the present invention improved needle cover assembly with the two halves in the open condition.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIG. 1, there is shown a preferred embodiment of the present invention needle cover assembly 2 which is connected to a conventional syringe 4. The connection of the needle cover assembly 2 to the syringe 4 may be by any conventional means such as a pushfit or threadedly mounted.

Referring to FIGS. 1, 2 and 3, the needle cover assembly 2 includes a hollow hub member 8, a rotatable collar 20 and an elongated cover member 10 which encloses a hypodermic needle 6. The hypodermic needle 6 and the hollow hub member 8 include a proximal end and a distal end. The needle cover assembly 2 utilizes the conventional female connecting portion which is connectable to the male connecting portion on a conventional syringe 4. The proximal end of the hollow hub member 8 is connectable to a male portion of the conventional syringe 4. The distal end of the hollow hub member 8 is connected to the proximal end of the hypodermic needle 6.

The elongated cover member 10 is split longitudinally into two unequal halves 16 and 18 which, in the closed position abut and are parallel to each other. In the open position, as shown in FIG. 2, the two halves 16 and 18 open to form a 90° opening for allowing the hypodermic needle 6 to inject the medicine into a patient. The two unequal halves 16 and 18 are split asymmetrically. Each half of the cover member 10 comprises a proximal end and a distal end. The distal end of the first half 16 has an arc shaped portion which is complementary to the distal end of the second half 18 and forms a hollow chamber completely enclosing the hypodermic needle 6. By way of example, the first half 16 of the cover member 10 is actually a 270° portion of a cylindrical dome top member and the second half 18 is the complementary 90° portion of the cylindrical dome top member. When the two halves 16 and 18 are closed, the two halves 16 and 18 form the complete cylindrical dome top member. The proximal ends of the two halves 16 and 18 are hingeably attached to the circumferential exterior sidewall 14 of the hollow hub member 8. The critical feature is that the large unequal half 16 has its distal end completely covering the needle 6 when in the closed position as shown in FIG. 1. In this way, a user cannot accidentally prick himself with the tip of the needle 6. It is emphasized that the selection of first half 16 being approximately a 270° arc cylinder and the second half 18 being approximately a 90° arc cylinder is one design choice. The key concept is that the larger unequal half 16 needs to have its dome portion cover the tip of the needle when in the closed position so a user cannot accidentally prick himself with the needle tip. In prior art needle covers, where the two halves are equal, there is a crack at the equal joinder location which is precisely where the tip of the needle is located and this allows someone to get pricked with the needle tip which is exactly at this location. The present invention eliminates this possibility.

A protruding flange 12 is integrally molded to the circumferential exterior sidewall 14 of the hollow hub member 8 and is located adjacent to the proximal end. The protruding flange 12 allows for pivotal movement of the two unequal halves 16 and 18 from a full vertical position to a 90° angle opening.

Referring to FIGS. 2, 4 and 5, the rotatable collar 20 comprises a top rim 22, a bottom rim 24 and a circumferential sidewall 26. The circumferential sidewall 26 includes a first recess notch 28 and an opposite second recess notch 30 which are located at the top rim 22. These recess notches 28 and 30 are utilized to allow the two halves 16 and 18 of the cover member 10 to open for exposing the hypodermic needle 6. The circumferential sidewall 26 comprises an exterior surface and an interior surface with a locking groove 32 which is located adjacent to the bottom rim 24 of the rotatable collar 20. The locking groove 32 extends between the two recess notches 28 and 30 which is about 90°, as illustrated in FIG. 5. When the rotatable collar 20 is assembled onto the hollow hub member 8, the locking groove 32 is tightly engaged with the protruding flange 12 of the hollow hub member 8. The interior sidewall of the rotatable member 20 conforms to the exterior sidewall 14 of the hollow hub member 8.

The hollow hub member 8, the elongated cover member 10 and the rotatable collar member 20 can be made by injection molding of plastic or any other suitable method.

In operation, when the rotatable collar 20 is rotated 90°, the two unequal halves 16 and 18 of the elongated cover member 10 are allowed to open into the two recess notches 28 and 30 on the top rim 22 of the rotatable collar member 20. When the rotatable collar 20 is rotated back, the two unequal halves 16 and 18 are forced back together by the top rim 22 of the rotatable collar member 20 to cover the hypodermic needle 6.

The present invention has many advantages over prior art needle caps in that at no point during the closing or opening procedures does the doctor or nurse or other user have to move their hand or fingers in the direction of the hypodermic needle point. As previously described, the hazard of someone's hand moving toward the needle point is eliminated. The opening and closing of the needle cap is by a simple rotation movement of the collar 20 and is a much safer procedure.

Referring to FIG. 6, there is shown a perspective view of an alternative embodiment of the present invention needle cover assembly 42 which can be connected to a conventional syringe, not shown. The connection of the needle cover assembly 42 to the syringe may be by any conventional means such as a pushfit or threadedly mounted.

There is a top plan view of the needle cover assembly 42 in the closed position shown in FIG. 7. The needle cover assembly 42 includes a hollow hub member 48, a rotatable collar member 60 and an elongated cover member 50 which encloses a hypodermic needle 46. The hypodermic needle 46 and the hollow hub member 48 include a proximal end and a distal end. The needle cover assembly 42 utilizes the conventional female connecting portion which is connectable to the male connecting portion on a conventional syringe. The proximal end of the hollow hub member 48 is connectable to a male portion of the conventional syringe. The distal end of the hollow hub member 48 is connected to the proximal end of the hypodermic needle 46.

The elongated cover member 50 is split longitudinally into two unequal halves 56 and 58 which, in the closed position, abut and are parallel to each other. In the open position shown in FIG. 8, the two halves 56 and 58 open to form a 180° opening perpendicular to the hypodermic needle 46 for allowing the hypodermic needle 46 to inject the medicine into a patient. The two halves 56 and 58 are split asymmetrically. Each half of the cover member 50 comprises a proximal end and a distal end. The distal end of the first half 56 has an arc shaped portion which is complementary to the distal end of the second half 58 and forms a hollow chamber completely enclosing the hypodermic needle 46. By way of example, the first half 56 of the cover member 50 is actually a 270° portion of a cylindrical dome top member and the second half 58 is the complementary 90° portion of the cylindrical dome top member. When the two halves 56 and 58 are closed, the two halves 56 and 58 form the complete cylindrical dome top member. The proximal ends of the two halves 56 and 58 are hingeably attached to the circumferential exterior sidewall 54 of the hollow hub member 48. The two halves 56 and 58 of the cover member 50 include two protruding flanges 52 and 53 which are integrally molded to the exterior surface. As with the first embodiment, the central feature is that the larger unequal half 56 has its distal end completely covering the needle 46 when in the closed position as shown in FIG. 6. In this way, a user cannot accidentally prick himself with the tip of the needle 6. As with the first embodiment, it is emphasized that the selection of first half 56 being approximately a 270° arc cylinder and the second half 58 being approximately a 90° arc cylinder is one design choice. The key concept is that the larger unequal half 56 needs to have its dome portion cover the tip of the needle when in the closed position so a user cannot accidentally prick himself with the needle tip.

Referring to FIGS. 7, 8 and 9, the rotatable collar member 60 comprises a top rim 62, a bottom rim 64 and a circumferential sidewall 66. The circumferential sidewall 66 includes a first recess notch 68 and an opposite second recess notch 70 which are located at the top rim 62 of the rotatable collar member 60. These recess notches 68 and 70 are utilized to allow the two halves 56 and 58 of the cover member 50 to open for exposing the hypodermic needle 46. The circumferential sidewall 66 comprises an exterior and an interior surface with a locking groove 72.

Referring to FIGS. 7 and 8, the locking groove 72 extends all around the interior surface of the circumferential sidewall 66 and is located adjacent and parallel to the top rim 62. To open the two halves 56 and 58 of the elongated cover member 50, the rotatable collar member 50 is rotated and the protruding flanges 52 and 53 of the two halves 56 and 58 engage with the locking groove 72. The protruding flanges 52 and 53 travel along the locking groove 72 of rotatable collar 60. At points 98, the locking groove 72 will be facing inwardly towards the two halves 56 and 58. At points 99, the locking groove 72 traverses and crosses over to the top rim 62. At points 100, the locking groove 72 will be facing upwardly. When the rotatable collar 60 is assembled onto the hollow hub member 48, the locking groove 72 is tightly engaged with the two protruding flange 52 and 53 of the two halves 56 and 58 of the cover member 50. The interior sidewall of the rotatable member 60 conforms to the exterior sidewall 54 of the hollow hub member 48.

The hollow hub member 48, the elongated cover member 50 and the rotatable collar member 60 can be made by injection molded plastic or other suitable method.

In operation, when the rotatable collar 60 is rotated 90°, the two halves 56 and 58 of the elongated cover member 50 are allowed to open into the two recess notches 68 and 70 by the two protruding flanges 52 and 53 travelling along the locking groove 72. When the rotatable collar 60 is rotated back, the two halves 56 and 58 are forced back together by the two recess notches 68 and 70 and also by the two protruding flanges 52 and 53 travelling along the locking groove 72.

Figure 14:
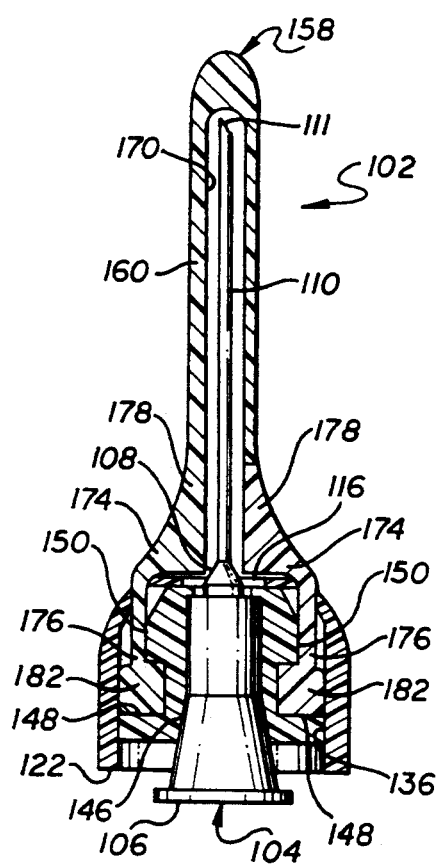
FIG. 14 is a partial cross-sectional view of the needle cover assembly.

Referring to FIGS. 10 and 14, there is shown a perspective view of another embodiment of the present invention improved needle cover assembly 102. The needle cover assembly 102 can be constructed out of four pieces: a frustum shaped base member 112, see FIG. 12; an elongated cover member which has a first half 160 and an opposite unequal second half 162; and a rotatable collar member or actuator enclosure 120.

The needle cover assembly 102 is used in conjunction with a conventional hollow hub member 104 which has a bottom end 106 connectable to a syringe and a top end 108 which is connected to a hypodermic needle 110 with a tip 111. By way of example, the syringe may be connected by any conventional means such as a pushfit or threadedly mounted. The needle cover assembly 102 can be manufactured with or without the hollow hub member 104. The needle cover assembly 102 is designed to be adaptable to any conventional hub member 104 which utilizes the hypodermic needle 110.

Figure 11:
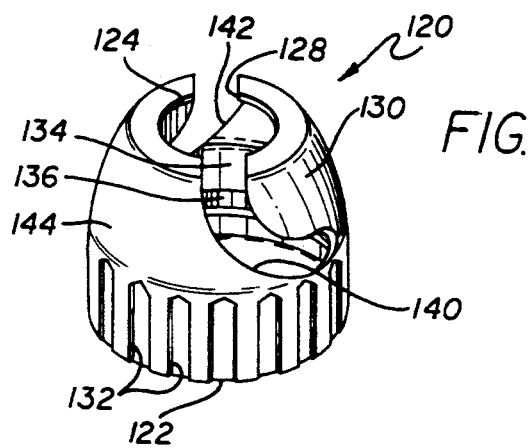
FIG. 11 is a perspective view of the rotatable collar member.

Referring to FIG. 11, there is shown a perspective view of the rotatable collar member 120. The rotatable collar member 120 has a top rim 124 with a central opening 128, a circumferential sidewall 130, and a bottom rim 122. The circumferential sidewall 130 has a knurled exterior surface 132 which is provided to facilitate the actuation of the rotatable collar member 120, and an interior surface 134 with an annular locking groove 136 which is located adjacent to the bottom rim 122. The circumferential sidewall 130 further has a first smooth curve or spiral shaped channel 140 and an opposite second smooth curve or spiral shaped channel 142. The pair of spiral shaped channels 140 and 142 are located opposite to each other and originate at the central opening 128 of the rotatable collar member 120. The pair of spiral channels 140 and 142 extend downwardly to a midsection 144 of the rotatable collar member 120 and allow the two unequal halves 160 and 162 of the elongated cover member to open for exposing the hypodermic needle 110, as shown in FIG. 10, or to be closed for protecting the hypodermic needle 110, as shown in FIG. 12.

Figure 12:
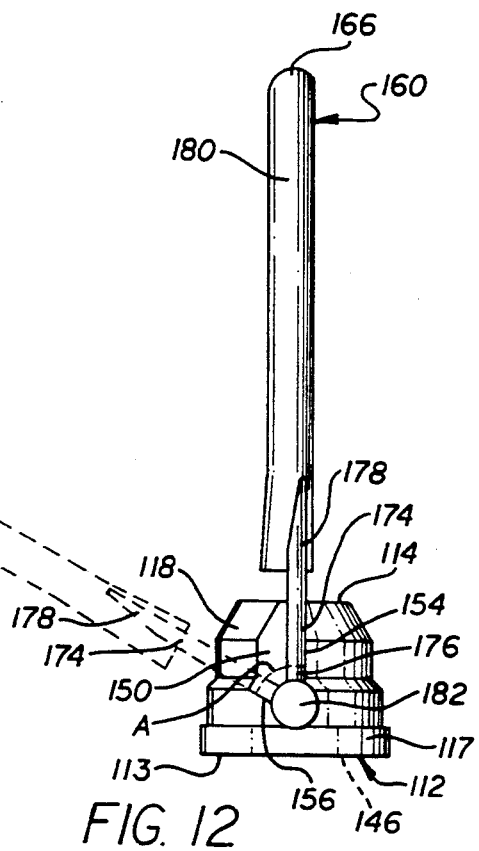
FIG. 12 is a side elevational view of the frustum shaped base and one of the two unequal halves of the cover member in the full vertical position, and also in the open condition shown in dashed lines.

Referring to FIGS. 12 and 14, the frustum shaped base member 112 has a top end 114 with a circular flange 116 which projects inwardly, a circumferential sidewall 118, a bottom end 113, and a hollow chamber 146 therethrough. The circumferential sidewall 118 has two small exterior voids 148 which are located opposite to each other and adjacent to the bottom end 113 of the base member 112. The circumferential sidewall 118 of the frustum shaped base member 112 is constructed with two vertical exterior plane surfaces 150 which are located opposite to each other and above a respective one of the two small exterior voids 148. Each vertical exterior plane surface 150 forms an acute angle A which is defined by a vertical edge 154 and an inclined edge 156. The acute angle A is approximately 85°.

Figure 13:
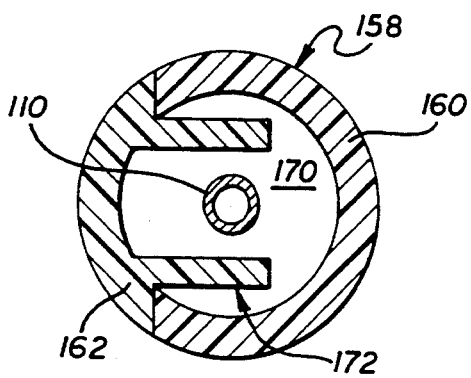
FIG. 13 is an enlarged cross-sectional view of the two unequal halves of the cover member.

Referring to FIGS. 10, 12, 13 and 14, the uniqueness of the needle cover assembly 102 is the elongated cover member 158 which is split longitudinally into two unequal halves 160 and 162 which, in the closed position abut and are parallel to each other, as shown in a cross-sectional view of FIG. 13. In the open position, as shown in FIG. 10, and FIG. 12 in dashed lines, the two halves 160 and 162 open to form approximately a 170° or more opening for allowing the hypodermic needle 110 to inject the medicine into a patient. The two unequal halves 160 and 162 are split asymmetrically. Each half of the cover member 158 has a top end 166 and a bottom end 164. The top end 166 of the first half 160 has an arc shaped portion which is complementary to the top end 166 of the second half 162 and forms a hollow chamber 170 completely enclosing the hypodermic needle 110. By way of example, the first half 160 of the cover member 158 is actually a 270° portion of a cylindrical dome top member and the second half 162 is the complementary 90° portion of the cylindrical dome top member. When the two halves 160 and 162 are closed, the two halves 160 and 162 form the complete cylindrical dome top member.

The second half 162 is designed with an arc shaped inner shell 172 which is similar to the shape of the first half 160 but with reduced dimensions such that the arc shaped inner shell 172 is completely enclosed by the first half 160 when in the closed position, as shown in FIG. 13. Both the arc shaped inner shell 172 of the second half 162 and the first half 160 provide a double protection to cover the hypodermic needle 110. The critical feature is that the large unequal half 160 and the arc shaped inner shell 172 of the second half 162 have their top ends 166 completely covering the needle 110 when in the closed position, as shown in FIG. 14. In this way, a user cannot accidentally prick himself or herself with the tip 111 of the needle 110. It is emphasized that the selection of first half 160 being approximately a 270° arc cylinder and the second half 162 being approximately a 90° arc cylinder with the arc shaped inner shell 172 is one design choice. The key concept is that two unequal halves 160 and 162 both cover the tip 111 of the needle 110 when in the closed position so a user cannot accidentally prick himself or herself with the needle tip 111.

Each half of the cover member 158 has an L-shaped arm 174. The L-shaped arms 174 are substantially identical, and to the extent they are, only one will be described in detail. The L-shaped arm 174 has a top end 178 and a bottom end 176 with a boss or a protuberance 182 projecting inwardly, where the top end 178 is integrally molded to a respective one side 180 of the two unequal halves 160 and 162 adjacent to the bottom ends 164. The L-shaped arms 174 allow for pivotal movement of the two unequal halves 160 and 162 from a full vertical position to an inclined position of approximately 85° opening for each half of the cover member 158.

The manufacturing process which could accommodate the construction of the needle cover assembly 102 can be injection, cast, thermoform, etc., or other molding processes. By way of example, the frustum shaped base member 112, the first and second halves 160 and 162 of the elongated cover member 158, and the rotatable collar member 120 can be made of plastic material or any other suitable material.

The needle cover assembly 102 is assembled by press-fitting the hollow hub member 104 into the hollow chamber 146 of the frustum shaped base member 112 such that the hypodermic needle 110 projects through the top end 114 of the frustum shaped base member 112. The circular flange 116 at the top end 114 of the frustum shaped base member 112 prevents the hollow hub member 104 from extending above the top end 114 of the base member 112. The bosses or protuberances 182 of the L-shaped arms 174 are inserted into a respective one of the two small exterior voids 148 of the circumferential sidewall 118 of the base member 112, where the rotatable collar member 120 is snapped onto to the circumferential sidewall 118 of the base member 112. The annular locking groove 136 engages with a protruding sidewall 117 adjacent to the bottom end 113 of the base member 112, thereby securing the rotatable collar member 120 and the first and second halves 160 and 162 of the cover member 158 to the frustum shaped base member 112.

The operation of the foregoing embodiment now will be described. When rotating the rotatable collar member 120, the L-shaped arms 174 of the first and second halves 160 and 162 of the elongated cover member 158 are allowed to travel downwardly along the first and second smooth curve shaped channels 140 and 142 respectively such that the incline edges 156 of the frustum shaped base member 112 can stop the downward movements of the first and second halves 160 and 162 of the cover member 158, and thereby the first and second halves 160 and 162 of the cover member 158 are open to expose the hypodermic needle 110. When the rotatable collar member 120 is rotated back, the L-shaped arms 174 of the first and second halves 160 and 162 of the cover member 158 are allowed to travel upwardly along the first and second smooth curve shaped channels 140 and 142 respectively such that the vertical edges 154 of the frustum shaped base member 112 stop the upward movements of the first and second halves 160 and 162 of the cover member 158, thereby covering the hypodermic needle 110.

Figure 15:
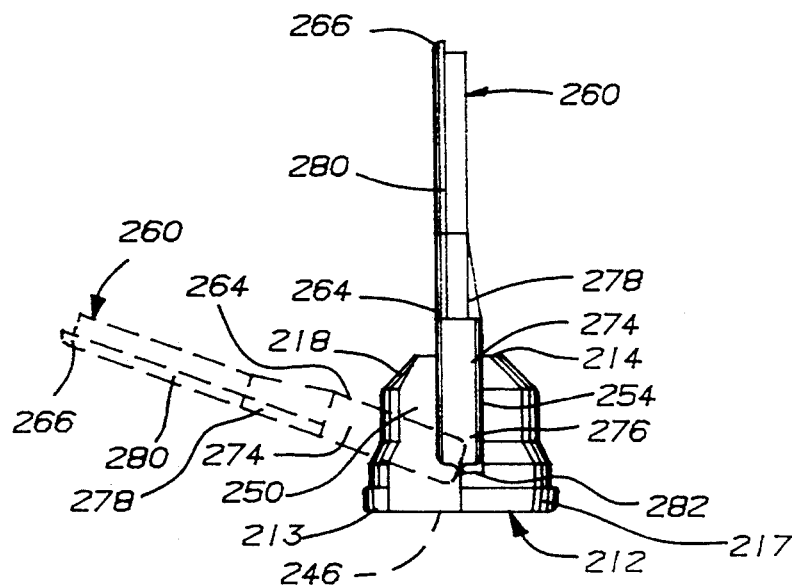
FIG. 15 is a side elevational view of another embodiment of the present invention, showing one of the two unequal halves of the cover member integrally attached by a living hinge to the frustum shaped base member in the full vertical position, and also in the open condition shown in dashed lines.
Figure 16:
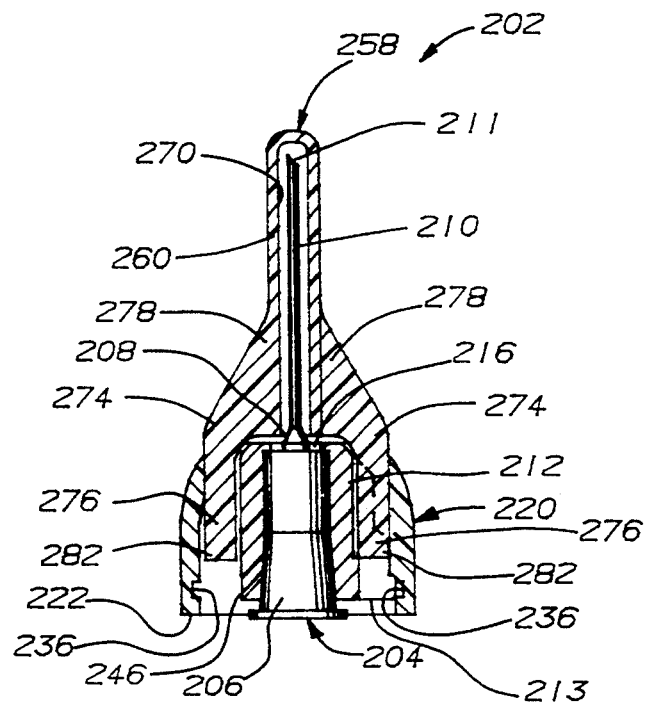
FIG. 16 is a partial cross-sectional view of the needle cover assembly showing the first and second halves of the cover member integrally and hingeably attached to the frustum shaped base member by living hinges.

Referring to FIGS. 15 and 16, there is shown another embodiment of the present invention improved needle cover assembly 202. The needle cover assembly 202 can be molded into two pieces: a frustum shaped base member 212; and a rotatable collar member or actuator enclosure 220. The frustum shaped base 212 further includes an elongated cover member which has a first half 260 and an opposite unequal second half (not shown in these figures but shown in FIG. 10). Since it is very similar to the previously described embodiment above except that the first and second halves of the cover member are integrally hinged to the frustum shaped base 212, the parts are numbered correspondingly with 200 added to each number.

The rotatable collar member 220 is exactly the same as the preceding embodiment, as shown in FIG. 11, and the description thereof will not be repeated. The frustum shaped base member 212 is very similar to the preceding embodiment, as shown in FIGS. 12 and 14, and the description thereof will not be repeated; only the modified parts will be described.

The circumferential sidewall 218 of the frustum shaped base 212 is constructed with two vertical exterior plane surfaces 250 which are located opposite to each other. Each vertical exterior plane surface 250 has a vertical edge 254.

Each half of the cover member 258 has an L-shaped arm 274. The L-shaped arms 274 are substantially identical, and to the extent they are, only one will be described in detail. The L-shaped arm 274 has a top end 278 and a bottom end 276, where the top end 278 is integrally molded to a respective one side 280 of the two unequal halves adjacent to the bottom ends 264. The bottom ends 276 of the L-shaped arms 274 are integrally hinged by living hinges 282 to a respective one of the vertical edges 254 of two vertical exterior plane surfaces 250 which allow for pivotal movement of the two unequal halves from a full vertical position to an inclined position of approximately 85° opening for each half of the cover member 258. These living hinges 282 are molded as part of the frustum shaped base member 212 and are preferably constructed from the same material as the needle cover assembly 202.

The manufacturing process which could accommodate the construction of the needle cover assembly 202 can be injection, cast, thermoform, etc., or other molding processes. By way of example, the frustum shaped base member 212, the first and second halves of the elongated cover member 258, and the rotatable collar member 220 can be made of plastic material or any other suitable material.

The needle cover assembly 202 is assembled by press-fitting the hollow hub member 204 into the hollow chamber 246 of the frustum shaped base member 212 such that the hypodermic needle 210 projects through the top end 214 of the frustum shaped base member 212. The circular flange 216 at the top end 214 of the frustum shaped base member 212 prevents the hollow hub member 204 from extending above the top end 214 of the base member 212. The rotatable collar member 220 is snapped onto the circumferential sidewall 218 of the base member 212, in which the annular locking groove 236 engages with a protruding sidewall 217 adjacent the bottom end 213 of the base member 212, thereby securing the rotatable collar member 220 to the frustum shaped base member 212.

The operation of the foregoing embodiment now will be described. When rotating the rotatable collar member 220, the L-shaped arms 274 of the first and second halves of the elongated cover member 258 are allowed to travel downwardly along the first and second smooth curve shaped channels respectively, and thereby open to expose the hypodermic needle 210. When the rotatable collar member 220 is rotated back, the L-shaped arms 274 of the first and second halves of the cover member 258 are allowed to travel upwardly along the first and second smooth curve shaped channels respectively such that the vertical edges 254 of the frustum shaped base member 212 stop the upward movements of the first and second halves of the cover member 258, thereby covering the hypodermic needle 210.

The present invention has many advantages over prior art needle caps in that at no point during the closing or opening procedures does the doctor or nurse or other user have to move their hand or fingers in the direction of the hypodermic needle point. As previously described, the hazard of someone's hand moving toward the needle point is eliminated. The opening and closing of the needle cover is by a simple rotational movement of the rotatable collar member and the needle cover provides a double protection.

Defined in detail, the present invention is a needle cover assembly used in conjunction with a hollow hub member, the hollow hub member having a bottom end connectable to a syringe and a top end connected to a hypodermic needle with a tip, the assembly comprising: (a) a rotatable collar member having a bottom rim, a top rim with a central opening, and a circumferential sidewall, the circumferential sidewall having a knurled exterior surface, an interior surface with an annular locking groove located adjacent to the bottom rim, a first smooth curve shaped channel, and an opposite second smooth curve shaped channel, each smooth curve shaped channel beginning at the top rim and extending downwardly to a midsection of the rotatable collar member; (b) a frustum shaped base member having a bottom end, a top end with a circular flange projecting inwardly, a circumferential sidewall, and a hollow chamber therethrough, the circumferential sidewall having two small exterior voids located at locations opposite to each other and adjacent to the bottom end and a protruding sidewall adjacent to the bottom end; (c) said circumferential sidewall of said frustum shaped base member further having two vertical exterior plane surfaces located at locations opposite to each other and each above a respective one of said two small exterior voids, each vertical exterior plane surface having an acute angle defined by a vertical edge and an inclined edge; (d) an elongated cover member having a first half and an opposite unequal second half, each half having a bottom end and a top end, the top end of the first half being arc shaped, the top end of the second half being complementary to the arc shaped top end of the first half, to form a hollow chamber enclosing said hypodermic needle; (e) said first half of said elongated cover member having a greater arc than said unequal second half of said elongated cover member such that said top end of said first half covers said tip of said hypodermic needle when in the closed position; (f) said unequal second half of said elongated cover member having an arc shaped inner shell similar to said first half of said cover member, the arc shaped inner shell having reduced dimensions such that the arc shaped inner shell is completely enclosed by said first half of said cover member when in the closed position and the arc shaped inner shell also covers said tip of said hypodermic needle for double protection; and (g) two L-shaped arms each having a bottom end and a top end, each top end integrally molded to a respective one of said bottom ends of said first and second halves of said cover member, each bottom end having a projecting boss for engaging with a respective one of said two small exterior voids of said circumferential sidewall of said frustum shaped base member, where said rotatable collar member can be snapped onto said frustum shaped base member such that said annular locking groove of said rotatable collar member engages with said protruding sidewall of said frustum shaped base member for securing said rotatable collar member and said first and second halves of said cover member to said frustum shaped base member; (h) whereby said hollow hub member is press-fitted through said hollow chamber of said frustum shaped base member such that said hypodermic needle projects through said top end of said frustum shaped base member and said circular flange prevents said top end of said hollow hub member from extending above said top end of said frustum shaped base member, and when rotating said rotatable collar member, said L-shaped arms of said first and second halves of said elongated cover member are allowed to travel downwardly along said first and second smooth curve shaped channels respectively such that said incline edges of said frustum shaped base member can stop the downward movements of said first and second halves of said cover member, and thereby said cover member is open to expose said hypodermic needle, and when said rotatable collar member is rotated back, said L-shaped arms of said first and second halves of said cover member are allowed to travel upwardly along said first and second smooth curve shaped channels respectively such that said vertical edges of said frustum shaped base member can stop the upward movements of said first and second halves of said cover member, and thereby cover said hypodermic needle.

Defined broadly, the present invention is a needle cover assembly used in conjunction with a hub member, the hub member having a bottom end connectable to a syringe and a top end connected to a hypodermic needle with a tip, the assembly comprising: (a) a collar member having a bottom rim, a top rim, and a sidewall, the sidewall having a first spiral shaped channel and an opposite second spiral shaped channel, each spiral shaped channel beginning at the top rim and extending downwardly to a midsection of the collar member; (b) a frustum shaped base member having a bottom end, a top end with a flange, a sidewall, and a hollow chamber therethrough, the sidewall having two small exterior voids and two exterior plane surfaces located at locations opposite to each other and adjacent to said bottom end of said frustum shaped base member, each exterior plane surface having a vertical edge and an inclined edge; (c) a cover member having a first half and an opposite unequal second half, the first half being complementary to the second half, to form a chamber enclosing said hypodermic needle; (d) said first half of said cover member having a greater arc than said unequal second half of said cover member such that said top end of said first half covers said tip of said hypodermic needle when in the closed position; (e) said unequal second half of said cover member having an inner shell with reduced dimensions such that the inner shell is completely enclosed by said first half of said cover member and the inner shell also covers said tip of said hypodermic needle when in the closed position for double protection; (f) a pair of L-shaped arms each having a bottom end and a top end, each top end integrally molded to a respective one of said bottom ends of said first and second halves of said cover member, each bottom end having a projecting boss for engaging with a respective one of said two small exterior voids of said sidewall of said frustum shaped base member; and (g) means for securing said collar member to said frustum shaped base member; (h) whereby said hub member is press-fitted through said hollow chamber of said frustum shaped base member such that said hypodermic needle projects through said top end of said frustum shaped base member and said flange prevents said top end of said hub member from extending above said top end of said frustum shaped base member, and when rotating said collar member, said L-shaped arms of said first and second halves of said cover member are allowed to travel downwardly along said first and second spiral channels respectively such that said inclined edges of said frustum shaped base member can stop the downward movements of said first and second halves, and thereby said cover member is open to expose said hypodermic needle, and when said collar member is rotated back, said L-shaped arms of said first and second halves are allowed to travel upwardly along said first and second spiral shaped channels respectively such that said vertical edges of said frustum shaped base member can stop the upward movements of said first and second halves, and thereby cover said hypodermic needle.

Defined more broadly, the present invention is a needle cover assembly used in conjunction with a hub member connectable to a syringe at one end and connected to a needle at the other end, the assembly comprising: (a) a collar member having a bottom rim, a top rim, and a sidewall, the sidewall having a pair of opposite spiral channels; (b) a base member having a first end, a second end, a sidewall, and a chamber such that said hub member can be inserted through the chamber, where said needle is projected through the first end of the base member; (c) a cover member having a first half and a second half, each half having a first end and a second end, each half having an arm with one end integrally molded to the second end of the cover half, and the other end of each arm having a protuberance; (d) means for securing said protuberances of said arms of said first and second halves to said base member; and (e) means for securing said collar member to said base member; (f) whereby when rotating said collar member, said arms of said first and second halves of said cover member are allowed to travel along said pair of spiral channels respectively to expose said needle, and when said collar member is rotated back, said arms of said first and second halves are allowed to travel along said pair of spiral channels respectively to cover said needle.

Alternatively defined in detail, the present invention is a needle cover assembly used in conjunction with a hollow hub member, the hollow hub member having a bottom end connectable to a syringe and a top end connected to a hypodermic needle with a tip, the assembly comprising: (a) a rotatable collar member having a bottom rim, a top rim with a central opening, and a circumferential sidewall, the circumferential sidewall having a knurled exterior surface, an interior surface with an annular locking groove located adjacent to the bottom rim, a first smooth curve shaped channel, and an opposite second smooth curve shaped channel, each smooth curve shaped channel beginning at the top rim and extending downwardly to a midsection of the rotatable collar member; (b) a frustum shaped base member having a bottom end, a top end with a circular flange projecting inwardly, a circumferential sidewall, and a hollow chamber therethrough, the circumferential sidewall having two vertical exterior plane surfaces located at locations opposite to each other and a protruding sidewall adjacent to the bottom end, each vertical exterior plane surface having a vertical edge; (c) an elongated cover member having a first half and an opposite unequal second half, each half having a bottom end and a top end, the top end of the first half being arc shaped, the top end of the second half being complementary to the arc shaped top end of the first half, to form a hollow chamber enclosing said hypodermic needle; (d) said first half of said elongated cover member having a greater arc than said unequal second half of said elongated cover member such that said top end of said first half covers said tip of said hypodermic needle when in the closed position; (e) said unequal second half of said elongated cover member having an arc shaped inner shell similar to said first half of said cover member, the arc shaped inner shell having reduced dimensions such that the arc shaped inner shell is completely enclosed by said first half of said cover member when in the closed position and the arc shaped inner shell also covers said tip of said hypodermic needle for double protection; and (f) two L-shaped arms each having a bottom end and a top end, each top end integrally molded to a respective one of said bottom ends of said first and second halves of said cover member, each bottom end integrally hinged by a living hinge to a respective one of said two vertical edges of said circumferential sidewall of said frustum shaped base member, where said rotatable collar member can be snapped onto said frustum shaped base member such that said annular locking groove of said rotatable collar member engages with said protruding sidewall of said frustum shaped base member for securing said rotatable collar member and said first and second halves of said cover member to said frustum shaped base member; (g) whereby said hollow hub member is press-fitted through said hollow chamber of said frustum shaped base member such that said hypodermic needle projects through said top end of said frustum shaped base member and said circular flange prevents said top end of said hollow hub member from extending above said top end of said frustum shaped base member, and when rotating said rotatable collar member, said L-shaped arms of said first and second halves of said elongated cover member are allowed to travel downwardly along said first and second smooth curve shaped channels respectively, and thereby said cover member is open to expose said hypodermic needle, and when said rotatable collar member is rotated back, said L-shaped arms of said first and second halves of said cover member are allowed to travel upwardly along said first and second smooth curve shaped channels respectively such that said vertical edges of said frustum shaped base member can stop the upward movements of said first and second halves of said cover member, and thereby cover said hypodermic needle.

Alternatively defined broadly, the present invention is a needle cover assembly used in conjunction with a hub member, the hub member having a bottom end connectable to a syringe and a top end connected to a hypodermic needle with a tip, the assembly comprising: (a) a collar member having a bottom rim, a top rim, and a sidewall, the sidewall having a first spiral shaped channel and an opposite second spiral shaped channel, each spiral shaped channel beginning at the top rim and extending downwardly to a midsection of the collar member; (b) a frustum shaped base member having a bottom end, a top end with a flange, a sidewall, and a hollow chamber therethrough, the sidewall having two exterior plane surfaces located at locations opposite to each, each exterior plane surface having a vertical edge; (c) a cover member having a first half and an opposite unequal second half, the first half being complementary to the second half, to form a chamber enclosing said hypodermic needle; (d) said first half of said cover member having a greater arc than said unequal second half of said cover member such that said top end of said first half covers said tip of said hypodermic needle when in the closed position; (e) said unequal second half of said cover member having an inner shell with reduced dimensions such that the inner shell is completely enclosed by said first half of said cover member and the inner shell also covers said tip of said hypodermic needle when in the closed position for double protection; (f) a pair of L-shaped arms each having a bottom end and a top end, each top end integrally molded to a respective one of said bottom ends of said first and second halves of said cover member respectively, each bottom end integrally hinged by a living hinge to a respective one of said two vertical edges of said sidewall of said frustum shaped base member; and (g) means for securing said collar member to said frustum shaped base member; (h) whereby said hub member is press-fitted through said hollow chamber of said frustum shaped base member such that said hypodermic needle projects through said top end of said frustum shaped base member and said flange prevents said top end of said hub member from extending above said top end of said frustum shaped base member, and when rotating said collar member, said L-shaped arms of said first and second halves of said cover member are allowed to travel downwardly along said first and second spiral shaped channels respectively, and thereby said cover member is open to expose said hypodermic needle, and when said collar member is rotated back, said L-shaped arms of said first and second halves are allowed to travel upwardly along said first and second spiral shaped channels respectively such that said vertical edges of said frustum shaped base member can stop the upward movements of said first and second halves, and thereby cover said hypodermic needle.

Alternatively defined more broadly, the present invention is a needle cover assembly used in conjunction with a hub member connectable to a syringe at one end and connected to a needle at the other end, the assembly comprising: (a) a collar member having a bottom rim, a top rim, and a sidewall, the sidewall having a pair of opposite spiral channels; (b) a base member having a first end, a second end, a sidewall, and a chamber such that said hub member is inserted through the chamber, where said needle is projected through the first end of the base member; (c) a cover member having a first half and a second half, each half having a first end and a second end, each half having an arm with one end integrally molded to a respective one of said second ends of said cover halves; (d) living hinge means for integrally attaching the other ends of said arms of said first and second halves to said base member; and (e) means for securing said collar member to said base member; (f) whereby when rotating said collar member, said arms of said first and second halves of said cover member are allowed to travel along said pair of spiral channels respectively to expose said needle, and when said collar member is rotated back, said arms of said first and second halves are allowed to travel along said pair of spiral channels respectively to cover said needle.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A needle cover assembly used in conjunction with a hollow hub member, the hollow hub member having a bottom end connectable to a syringe and a top end connected to a hypodermic needle with a tip, the assembly comprising:

a. a rotatable collar member having a bottom rim, a top rim with a central opening, and a circumferential sidewall, the circumferential sidewall having a knurled exterior surface, an interior surface with an annular locking groove located adjacent to the bottom rim, a first smooth curve shaped channel, and an opposite second smooth curve shaped channel, each smooth curve shaped channel beginning at the top rim and extending downwardly to a midsection of the rotatable collar member;

b. a frustum shaped base member having a bottom end, a top end with a circular flange projecting inwardly, a circumferential sidewall, and a hollow chamber therethrough, the circumferential sidewall having two small exterior voids located at locations opposite to each other and adjacent to the bottom end and a protruding sidewall adjacent to the bottom end;

c. said circumferential sidewall of said frustum shaped base member further having two vertical exterior plane surfaces located at locations opposite to each other and each above a respective one of said two small exterior voids, each vertical exterior plane surface having an acute angle defined by a vertical edge and an inclined edge;

d. an elongated cover member having a first half and an opposite unequal second half, each half having a bottom end and a top end, the top end of the first half being arc shaped, the top end of the second half being complementary to the arc shaped top end of the first half, to form a hollow chamber enclosing said hypodermic needle;

e. said first half of said elongated cover member having a greater arc than said unequal second half of said elongated cover member such that said top end of said first half covers said tip of said hypodermic needle when in the closed position;

f. said unequal second half of said elongated cover member having an arc shaped inner shell similar to said first half of said cover member, the arc shaped inner shell having reduced dimensions such that the arc shaped inner shell is completely enclosed by said first half of said cover member when in the closed position and the arc shaped inner shell also covers said tip of said hypodermic needle for double protection; and g. two L-shaped arms each having a bottom end and a top end, each top end integrally molded to a respective one of said bottom ends of said first and second halves of said cover member, each bottom end having a projecting boss for engaging with a respective one of said two small exterior voids of said circumferential sidewall of said frustum shaped base member, where said rotatable collar member can be snapped onto said frustum shaped base member such that said annular locking groove of said rotatable collar member engages with said protruding sidewall of said frustum shaped base member for securing said rotatable collar member and said first and second halves of said cover member to said frustum shaped base member;

h. whereby said hollow hub member is press-fitted through said hollow chamber of said frustum shaped base member such that said hypodermic needle projects through said top end of said frustum shaped base member and said circular flange prevents said top end of said hollow hub member from extending above said top end of said frustum shaped base member, and when rotating said rotatable collar member, said L-shaped arms of said first and second halves of said elongated cover member are allowed to travel downwardly along said first and second smooth curve shaped channels respectively such that said incline edges of said frustum shaped base member can stop the downward movements of said first and second halves of said cover member, and thereby said cover member is open to expose said hypodermic needle, and when said rotatable collar member is rotated back, said L-shaped arms of said first and second halves of said cover member are allowed to travel upwardly along said first and second smooth curve shaped channels respectively such that said vertical edges of said frustum shaped base member can stop the upward movements of said first and second halves of said cover member, and thereby cover said hypodermic needle.

2. The invention as defined in claim 1 wherein said frustum shaped base member, said first and second halves of said elongated cover member, and said rotatable collar member are made of injection molded plastic.

3. The invention as defined in claim 1 wherein said acute angles of said circumferential exterior sidewall of said frustum shaped base member are approximately 85°.

4. A needle cover assembly used in conjunction with a hub member, the hub member having a bottom end connectable to a syringe and a top end connected to a hypodermic needle with a tip, the assembly comprising:

a. a collar member having a bottom rim, a top rim, and a sidewall, the sidewall having a first spiral shaped channel and an opposite second spiral shaped channel, each spiral shaped channel beginning at the top rim and extending downwardly to a midsection of the collar member;

b. a frustum shaped base member having a bottom end, a top end with a flange, a sidewall, and a hollow chamber therethrough, the sidewall having two small exterior voids and two exterior plane surfaces located at locations opposite to each other and adjacent to said bottom end of said frustum shaped base member, each exterior plane surface having a vertical edge and an inclined edge;

c. a cover member having a first half and an opposite unequal second half, the first half being complementary to the second half, to form a chamber enclosing said hypodermic needle;

d. said first half of said cover member having a greater arc than said unequal second half of said cover member such that said top end of said first half covers said tip of said hypodermic needle when in the closed position;

e. said unequal second half of said cover member having an inner shell with reduced dimensions such that the inner shell is completely enclosed by said first half of said cover member and the inner shell also covers said tip of said hypodermic needle when in the closed position for double protection;

f. a pair of L-shaped arms each having a bottom end and a top end, each top end integrally molded to a respective one of said bottom ends of said first and second halves of said cover member, each bottom end having a projecting boss for engaging with a respective one of said two small exterior voids of said sidewall of said frustum shaped base member; and g. means for securing said collar member to said frustum shaped base member;

h. whereby said hub member is press-fitted through said hollow chamber of said frustum shaped base member such that said hypodermic needle projects through said top end of said frustum shaped base member and said flange prevents said top end of said hub member from extending above said top end of said frustum shaped base member, and when rotating said collar member, said L-shaped arms of said first and second halves of said cover member are allowed to travel downwardly along said first and second spiral channels respectively such that said inclined edges of said frustum shaped base member can stop the downward movements of said first and second halves, and thereby said cover member is open to expose said hypodermic needle, and when said collar member is rotated back, said L-shaped arms of said first and second halves are allowed to travel upwardly along said first and second spiral shaped channels respectively such that said vertical edges of said frustum shaped base member can stop the upward movements of said first and second halves, and thereby cover said hypodermic needle.

5. The invention as defined in claim 4 wherein said frustum shaped base member, said first and second halves of said cover member, and said collar member are made of injection molded plastic.

6. The invention as defined in claim 4 wherein said means for securing said collar member to said frustum shaped base member includes an annular locking groove located at a location adjacent to said bottom rim of said collar member such that the annular locking groove engages with a protruding sidewall located adjacent to said bottom end of said frustum shaped base member, where said collar member is snapped onto said frustum shaped base member, and thereby secures said collar member, and said first and second halves of said cover member to said frustum shaped base member.

7. The invention as defined in claim 4 wherein said sidewall of said collar member has knurled exterior surfaces for gripping said collar member.

8. A needle cover assembly used in conjunction with a hub member connectable to a syringe at one end and connected to a needle at the other end, the assembly comprising:

a. a collar member having a bottom rim, a top rim, and a sidewall, the sidewall having a pair of opposite spiral channels;

b. a base member having a first end, a second end, a sidewall, and a chamber such that said hub member can be inserted through the chamber, where said needle is projected through the first end of the base member;

c. a cover member having a first half and a second half, each half having a first end and a second end, each half having an arm with one end integrally molded to the second end of the cover half, and the other end of each arm having a protuberance;

d. means for securing said protuberances of said arms of said first and second halves to said base member; and e. means for securing said collar member to said base member;

f. whereby when rotating said collar member, said arms of said first and second halves of said cover member are allowed to travel along said pair of spiral channels respectively to expose said needle, and when said collar member is rotated back, said arms of said first and second halves are allowed to travel along said pair of spiral channels respectively to cover said needle.

9. The invention as defined in claim 8 wherein said base member includes a flange at said first end for preventing said hub member from extending above said first end of said base member.

10. The invention as defined in claim 8 wherein said second half of said cover member includes an inner shell with reduced dimensions such that the inner shell is completely enclosed by said first half and the inner shell also covers said tip of said needle when in the closed position for double protection.

11. The invention as defined in claim 8 wherein said means for securing said protuberances of said arms of said first and second halves to said base member includes two small exterior voids located opposite to each other on said sidewall, and two exterior plane surfaces located opposite to each other and each above a respective one of the two small exterior voids, each exterior plane surface having an acute angle defined by a vertical edge and an inclined edge.

12. The invention as defined in claim 11 wherein said acute angles of said sidewall of said base member are approximately 85°.

13. The invention as defined in claim 8 wherein said means for securing said collar member to said base member includes a locking groove which is located adjacent to said bottom rim of said of collar member and engages with a protruding sidewall adjacent to said second end of said base member, where said collar member is snapped onto said base member for securing said first and second halves of said cover member to said base member.

* * * * *